(12) United States Patent
Boubia et al.

(10) Patent No.: US 8,575,210 B2
(45) Date of Patent: Nov. 5, 2013

(54) USE OF INDOLE DERIVATIVES AS NURR-1 ACTIVATORS FOR TREATING PARKINSON'S DISEASE

(75) Inventors: Benaïssa Boubia, Saint Apollinaire (FR); Johannes Bernard Van Vliet, Hilversum (NL); Joseph Antonius Jacobus Den Hartog, Weesp (NL); Andrew McCreary, Almere (NL); Mireille Tallandier, Bretigny (FR); Petronella Johanna Maria Van Dongen, Hilversum (NL); Olivia Poupardin-Olivier, Varois Et Chaignot (FR)

(73) Assignee: Laboratoires Fournier SA, Dijon (FR)

( * ) Notice: Subject to any disclaimer, the term of this patent is extended or adjusted under 35 U.S.C. 154(b) by 96 days.

(21) Appl. No.: 13/003,554

(22) PCT Filed: Jul. 9, 2009

(86) PCT No.: PCT/FR2009/051372
§ 371 (c)(1),
(2), (4) Date: Apr. 6, 2011

(87) PCT Pub. No.: WO2010/004221
PCT Pub. Date: Jan. 14, 2010

(65) Prior Publication Data
US 2011/0178150 A1 Jul. 21, 2011

(30) Foreign Application Priority Data
Jul. 10, 2008 (FR) ...................................... 08 54712

(51) Int. Cl.
*A61K 31/405* (2006.01)
*C07D 209/04* (2006.01)

(52) U.S. Cl.
USPC .......................................... 514/415; 548/469

(58) Field of Classification Search
USPC ....................................................... 548/469
See application file for complete search history.

(56) References Cited

U.S. PATENT DOCUMENTS

| 2009/0143420 A1 | 6/2009 | Peyronel et al. |
| 2009/0143421 A1 | 6/2009 | Peyronel |
| 2009/0253735 A1 | 10/2009 | Almario-Garcia et al. |
| 2010/0168155 A1 | 7/2010 | El-Ahmad et al. |
| 2010/0286137 A1 | 11/2010 | Binet et al. |

FOREIGN PATENT DOCUMENTS

| FR | 2 890 071 A1 | 3/2007 |
| FR | 2 903 105 A1 | 1/2008 |
| FR | 2 903 106 A1 | 1/2008 |
| FR | 2 903 107 A1 | 1/2008 |
| WO | WO 03/015780 A2 | 2/2003 |
| WO | WO 2004/072050 A1 | 8/2004 |
| WO | WO 2005/056522 A2 | 6/2005 |
| WO | WO 2008/034974 A1 | 3/2008 |

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http://www.cnn.com/2003/HEALTH/conditions/O9/24/alzheimers.drug.ap/indexhtml>.*
Binet, et al. Document 146:295771, (2007) retrieved from CAPLUS.*
PCT/ISA/210 form with translation dated Mar. 15, 2010 (ten (10) pages).
PCT/ISA/237 form dated Jul. 9, 2009 (seven (7) pages).
Dubois et al., Identification of a Potent Agonist of the Orphan Nuclear Receptor Nurr1, Chem Med Chem, Sep. 2006, pp. 955-958, vol. 1.
Guonqiang Xing et al., Reduction of dopamine-related transcription factors Nurr 1 and NGF1-B in the prefrontal cortex ni schizophrenia and bipoloar disorders, Schizophrenia Research 84, 2006, pp. 36-56.
Ines Ancin et al., NR4A2: Effectis of an "Orphan" Receptor on Sustained Attention in a Schizophrenic Population, Schizophrenia Bulletin Advance Access, Jan. 31, 2012.
Mamma Al Banchaabouchi et al., Chronic lithium decreases Nurr1 expression in the rat brain and impairs spatial discrimination, Pharmacology, Biochemistry and Behavior 79, 2004, pp. 607-621.

(Continued)

*Primary Examiner* — Shawquia Young
(74) *Attorney, Agent, or Firm* — Crowell & Moring LLP

(57) ABSTRACT

The present invention relates to a compound derived from indole, especially a therapeutically useful compound, characterized in that it is selected from compounds of formula (I)

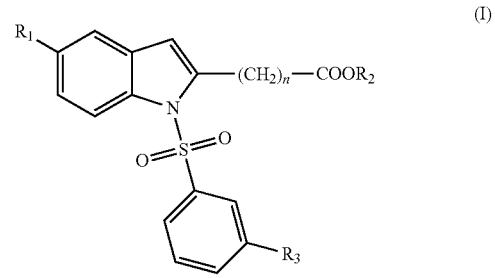

(I)

in which
$R_1$ represents a halogen or a trifluoromethyl group,
$R_2$ represents a hydrogen atom or a $C_1$-$C_4$ alkyl group,
$R_3$ represents an isopropyl (1-methylethyl) group or a tert-butyl (1,1-dimethylethyl) group and
n=3 or 4
and
pharmaceutically acceptable salts of said compounds of formula (I).
Application: Treatment of neurodegenerative diseases and more particularly of Parkinson's disease.

9 Claims, 2 Drawing Sheets

(56) References Cited

OTHER PUBLICATIONS

Stephanie Vuillermot et al., Prenatal Immune Activation Interacts with Genetic Nurr 1 Deficiency in the Development of Attentional Impairments, The Journal of Neuroscience, Jan. 11, 2012, 32(2) pp. 436-451.

Wanda I. Colon-Cesario et al., Knockdown of Nurr1 in the rat hippocampus: Implications to spatial discrimination learning and memory, Learning & Memory, 13, pp. 734-744, Nov. 17, 2009.

Yaping Chu et al., Nurr1 in Parkinson's disease and related disorders, J. Comp. Heurol. Jan. 20, 2006, 494(3): 495-514.

* cited by examiner

USE OF INDOLE DERIVATIVES AS NURR-1 ACTIVATORS FOR TREATING PARKINSON'S DISEASE

The present invention relates to a new therapeutic use of certain indole derivatives in the treatment and/or prevention of diseases involving the nuclear receptors NURR-1. More specifically this invention relates to the use of these compounds for preparing a medicament for the treatment and/or prevention of Parkinson's disease.

BACKGROUND OF THE INVENTION

Neurodegenerative diseases are defined as being diseases characterized by progressive dysfunction of the nervous system. They are often associated with atrophy of the structures of the central or peripheral nervous system that is affected. They include, among others, diseases such as Alzheimer's disease, Creutzfeldt-Jakob disease, Huntington's disease, Parkinson's disease, lysosomal diseases, progressive supranuclear palsy, multiple sclerosis and amyotrophic lateral sclerosis. Among neurodegenerative diseases, Parkinson's disease is an affliction which affects around four million people worldwide. Although affecting individuals of any age, it is most common in older people (with 2% of the population of people older than 65 years being affected by this disease). It is characterized by degeneration of the dopaminergic neurons of the substantia nigra.

Dopamine is a neurotransmitter which plays a central part in the control of voluntary movements, in cognitive functions and in the development of behaviours associated with the emotions.

The current therapeutic strategy for the treatment of Parkinson's disease resides in attenuating the symptoms by compensating the dopamine deficiency through the administration of a metabolic precursor such as L-DOPA.

Presently, the increase in the frequency of this pathology has made it necessary to develop new therapeutic agents which play a beneficial part in neuronal differentiation and survival.

This development has led to the identification of compounds which are capable of activating the nuclear receptors involved in the pathogenesis of Parkinson's disease.

Highly expressed in the brain, the transcription factor NURR-1, a member of the orphan nuclear receptor superfamily, has been identified as having an essential role in the development and maintenance of the dopaminergic neurons of the mesencephalon (Zetterstrom, Solomin and al. 1997, *Science.* 1997 Apr. 11; 276(5310):248-50).

The NURR-1 nuclear receptor intervenes in the maintenance of the dopaminergic phenotype via the regulation of specific genes of the dopaminergic (DA) neurons. It also favours the survival of the DA neurons by protecting them from toxic attacks. The NURR-1 nuclear receptor therefore acts as a specific transcription factor of the dopaminergic neurons, whose activities it will be possible to regulate by modulation of dopaminergic neurotransmission in Parkinson's disease.

This receptor binds to DNA in the form of monomers, homodimers or heterodimers with RXR (Retinoid X Receptor), a nuclear receptor which is a heteropartner to many other members of the nuclear receptor family. RXR intervenes in many physiological processes, such as lipid metabolism, glucose metabolism, development and differentiation. NURR-1 thus interacts with the α and γ isoforms of RXR. The expression of RXRα is ubiquitous, whereas that of RXRγ is concentrated primarily in the brain and more particularly in the striatum, the hypothalamus and the hypophysis.

The NURR-1/RXRα and NURR-1/RXRγ complexes formed are capable of regulating transcription in reponse to a ligand of RXR. RXR therefore positively modulates the potential for activation of the transcription of NURR-1.

Identifying compounds capable of inducing the activity of the NURR-1/RXRα and NURR-1/RXRγ complexes ought therefore to allow new pathways to be made available for the treatment of Parkinson's disease.

Document WO2003/015780 discloses heterocyclic compounds which are active for the treatment of Parkinson's disease.

Furthermore, documents WO2004/072050, FR 2 903 105, FR 2 903 106 and FR 2 903 107 describe compounds which are activators of the NURR-1 receptor, while the use of heterocyclic compounds which modulate the activity of receptors of the NGFI-B family (of which NURR-1 is a member) is described in document WO2005/047268.

Lastly, document WO2005/056522 discloses indole derivatives which are activators of the PPAR nuclear receptors and find application as active principles of medicaments for the treatment of certain diseases of the cardiovascular system.

In this context it has been found—and it is this which constitutes the basis of the present invention—that certain compounds derived from indole and embraced by the general formula given in document WO2005/056522 are selective NURR-1/RXRα and NURR-1/RXRγ agonists which are capable of inhibiting the degeneration of neurons that is observed in Parkinson's disease.

Hence it has been shown that, surprisingly, the compounds of the invention, further to their PPAR activator power, exhibit a very high potential for activation of the NURR-1/RXRα and NURR-1/RXRγ heterodimers. These compounds, therefore, by virtue of their unique properties, are of particular interest with respect to their use in the treatment or prevention of diseases involving the NURR-1 receptor, especially of neurodegenerative diseases and more particularly of Parkinson's disease.

Accordingly the present invention first provides, as new products, compounds derived from indole, selected from i) compounds of formula (I)

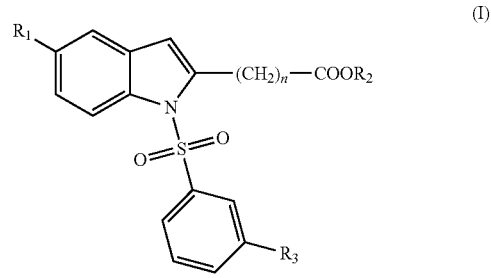

in which
$R_1$ represents a halogen or a trifluoromethyl group,
$R_2$ represents a hydrogen atom or a $C_1$-$C_4$ alkyl group,
$R_3$ represents an isopropyl (1-methylethyl) group or a tert-butyl (1,1-dimethylethyl) group and
n=3 or 4
and
ii) pharmaceutically acceptable salts of said compounds of formula (I).

It has been observed—and this is the original nature of the compounds of the invention—that the simultaneous presence:

- of an isopropyl substituent or of a tert-butyl substituent in meta position on the benzenesulphonyl group; and
- of a halogen or of a trifluoromethyl group in position 5 of the indole endows the compounds of the invention with a remarkable and entirely unexpected activity with regard to NURR-1 receptors.

The compounds of the invention therefore have a chemical structure which, although covered generally by the general formula described in document WO 2005/056522, is the result of a selection which a person skilled in the art would not have been able to carry out in searching for compounds intended for the treatment of Parkinson's disease.

The invention secondly provides the aforementioned compounds for their use as pharmacologically active substances, and also the pharmaceutical compositions comprising them.

The invention thirdly provides for the use of at least one compound of formula (I) or one of its pharmaceutically acceptable salts as an active principle for preparing a medicament intended for the treatment of diseases involving the NURR-1 receptor, especially neurodegenerative diseases, such as, more particularly, Parkinson's disease.

DETAILED DESCRIPTION

Figure 1:
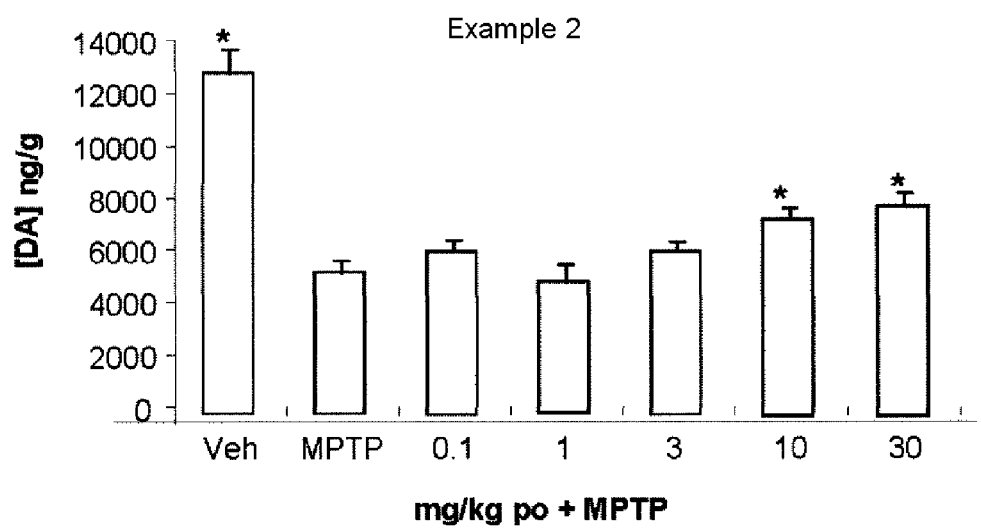
FIGS. 1, 2 and 3 are graphs depicting the results of tests of experiments demonstrating the pharmacological activity of respresentative compounds according to the invention.

In the present description, a $C_1$-$C_4$ alkyl group is a linear or branched, saturated hydrocarbon chain having 1 to 4 carbon atoms, and more particularly a methyl, ethyl, propyl, 1-methylethyl, butyl, 1-methylpropyl, 2-methylpropyl or 1,1-dimethylethyl group.

A halogen is a fluorine or chlorine atom.

The compounds of formula (I) in which $R_2$ represents a hydrogen atom are carboxylic acids, which can be used in the free acid form or in the form of salts, said salts being obtained by combining the acid with a non-toxic organic or inorganic base which is preferably pharmaceutically acceptable. Inorganic bases which can be used include, for example, sodium hydroxide, potassium hydroxide, magnesium hydroxide or calcium hydroxide. Organic bases which can be used include, for example, amines, amino alcohols, basic amino acids such as lysine or arginine, or else compounds which carry a quaternary ammonium function, such as betaine or choline, for example.

The compounds according to the invention may be prepared by a first process involving:

a) reacting the compound of formula (II)

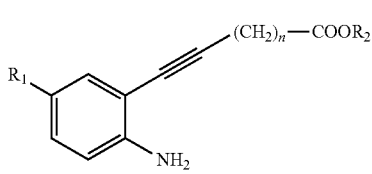

(II)

in which
$R_1$ represents a halogen or a trifluoromethyl group,
$R_2$ represents a hydrogen atom or a $C_1$-$C_4$ alkyl group and
n=3 or 4
with a benzenesulphonyl chloride of formula (III)

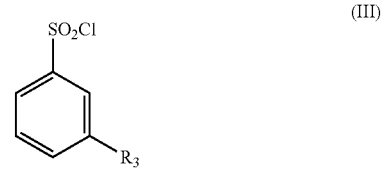

(III)

in which
$R_3$ represents an isopropyl or test-butyl group
in the presence of a solvent and a base, such as, for example, pyridine, at ambient temperature, for approximately 15 hours, to give the compound of formula:

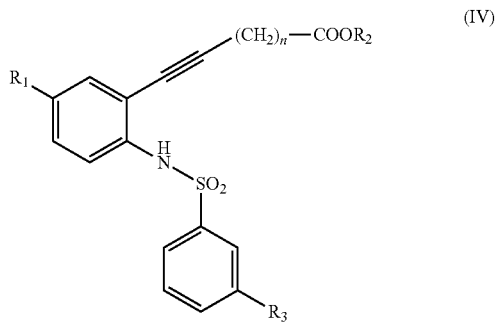

(IV)

in which
$R_1$, $R_2$, $R_3$ and n retain the same meaning as in the starting compounds;

b) carrying out cyclization of the compound of formula (IV), for example by the action of copper(II) acetate (see for example J. Org. Chem., 2004, 69 (4), 1126-1136), in a solvent such as 1,2-dichloroethane at a temperature close to the reflux temperature of the solvent, for approximately 15 hours, to give the compound of formula

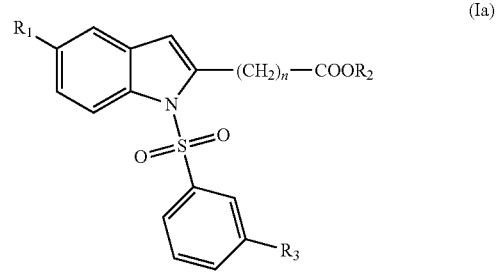

(Ia)

in which
$R_1$, $R_2$, $R_3$ and n retain the same meaning as in the starting compound;

c) if necessary, hydrolysing the ester function of the compound of formula (Ia), for example by the action of an inorganic base such as lithium hydroxide, according to procedures which are well known to a person skilled in the art, to give, after acid treatment, the compound of formula (I) in its free acid form:

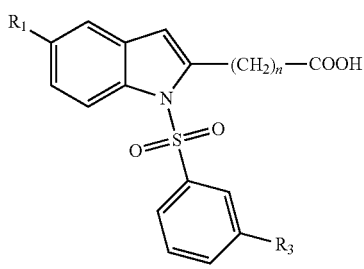

(Ib)

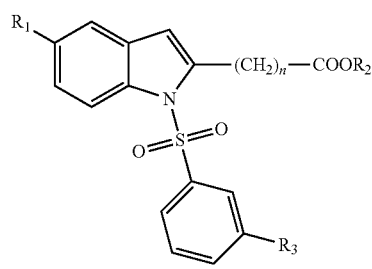

(Ia)

In a first variant, the compounds of formula (I) may be obtained by a process involving:

a) cyclizing the compound of formula

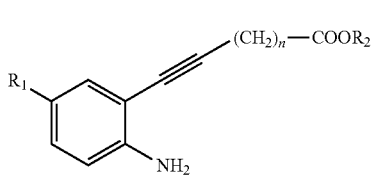

(II)

in which $R_1$ represents a halogen or a trifluoromethyl group, $R_2$ represents a hydrogen atom or a $C_1$-$C_4$ alkyl group and n=3 or 4 under conditions similar to those described for carrying out step b) of the general process above, to give the indole compound of formula

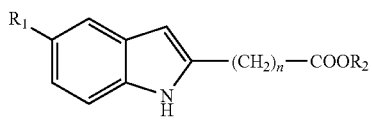

(V)

in which $R_1$, $R_2$ and n retain the same meaning as in the starting compound;

b) reacting the compound of formula (V) with a benzenesulphonyl chloride of formula (III)

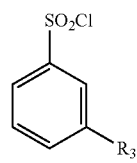

(III)

in which $R_3$ represents an isopropyl or tert-butyl group, in a solvent such as, for example, dimethylformamide (DMF), at ambient temperature for approximately 3 hours, after activation of the indole compound of formula (V) with sodium hydride, to give the compound of formula (Ia)

in which $R_1$, $R_2$, $R_3$ and n retain the same meaning as in the starting compound;

c) hydrolysing, if necessary, the ester function of the compound of formula (Ia), for example (in the case of a tert-butyl ester) by the action of an organic acid such as trifluoroacetic acid, in a solvent such as dichloromethane, according to procedures which are well known to a person skilled in the art, to give the compound of formula (I) in its free acid form:

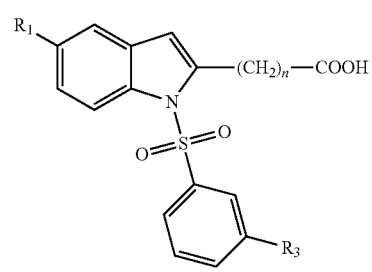

(Ib)

In a second variant, the compounds of formula (I) may be obtained by a process involving:

a) reacting the compound of formula (VI)

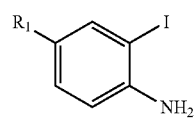

(VI)

in which $R_1$ represents a halogen or a trifluoromethyl group with a benzenesulphonyl chloride of formula (III)

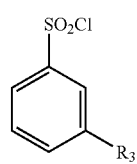

(III)

in which $R_3$ represents an isopropyl or tert-butyl group, in a solvent such as, for example, pyridine, at ambient temperature for 4 hours, to give the compound of formula (VII)

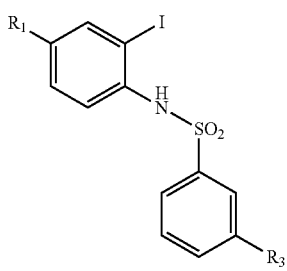

in which
$R_1$ and $R_3$ retain the same meaning as in the starting compounds;

b) reacting the compound of formula (VII) with an acetylene derivative of formula

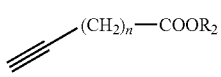

in which
$R_2$ represents a hydrogen atom or a $C_1$-$C_4$ alkyl group,
n=3 or 4;
in the presence of cuprous iodide, a palladium-based catalyst such as, for example, bis(triphenylphosphine)palladium chloride, and an organic base such as, for example, triethylamine, in a solvent such as, for example, dimethylformamide (DMF) at a temperature between the ambient temperature and 80° C. for 12 hours, to give the compound of formula

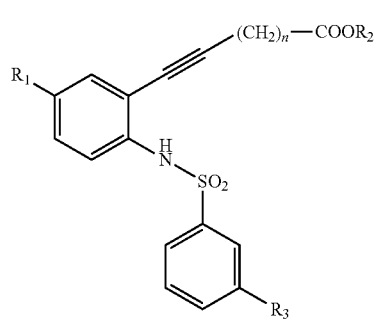

in which $R_1$, $R_2$, $R_3$ and n retain the same meaning as in the starting compounds;

c) cyclizing the compound of formula (IV) above, under conditions similar to those described for carrying out step (b) of the general process above, to give the indole compound of formula

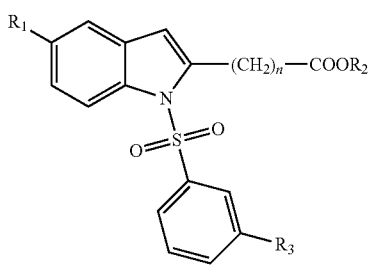

in which
$R_1$, $R_2$, $R_3$ and n retain the same meaning as in the starting compound;

d) hydrolysing, if necessary, the ester function of the compound of formula Ia, for example (in the case of a tert-butyl ester) by the action of an organic acid such as trifluoroacetic acid, in a solvent such as dichloromethane, according to procedures which are well known to a person skilled in the art, to give the compound of formula I in its free acid form:

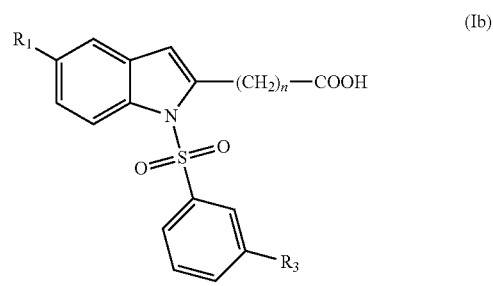

in which
$R_1$, $R_2$, $R_3$ and n retain the same meaning as in the starting compound.

It should be noted that, under certain conditions, steps b) and c) of this process may advantageously be carried out in a single operation (a so-called one pot process).

The compound of formula (II) in which $R_1$ represents a halogen or a trifluoromethyl group, $R_2$ represents a $C_1$-$C_4$ alkyl group and n represents 3 or 4 may be obtained by reacting an ortho-iodoaniline of formula

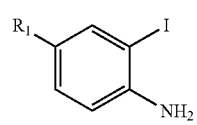

with an alkynoic ester of formula

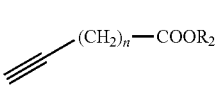

in which
$R_2$ represents a $C_1$-$C_4$ alkyl group and
n=3 or 4;
in the presence of cuprous iodide, a palladium-based catalyst such as, for example, bis(triphenylphosphine)palladium chloride, and an organic base such as, for example, triethylamine, in a solvent such as, for example, dimethylformamide (DMF) at a temperature between the ambient temperature and 80° C. for 1 to 12 hours.

The alkynoic ester of formula

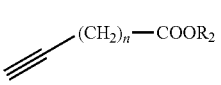

in which
$R_2$ represents a $C_1$-$C_4$ alkyl group and
n=3 or 4
may be obtained by starting from the corresponding alkynoic acid, by successive action of oxalyl chloride and then of a metal alkoxide of formula R₂OM in which M represents an alkali metal such as, for example, sodium or potassium.

The compounds of the invention in the form of salts of an acid of formula (Ib) with an organic or inorganic base may be obtained in conventional manner, using the methods which are well known to a person skilled in the art, for example by mixing stoichiometric amounts of the acid of formula (Ib) and the base in a solvent, such as, for example, water or an aqueous-alcoholic mixture, and by then lyophilizing the resulting solution.

In some of the reaction steps described above, it is possible advantageously to replace the traditional heating methods by microwave heating using reactors that are suitable for this type of reaction. In this case a person skilled in the art will understand that the heating times will be considerably reduced by comparison with the times needed in the case of conventional heating.

The following examples of preparation of compounds according to the formula (I) will allow better understanding of the invention.

In these examples, which do not limit the scope of the invention, the examples titled "preparation" are examples describing the synthesis of intermediates, and those titled "examples" describe the synthesis of compounds of formula (I) according to the invention.

The following abbreviations have been used:

mM: millimole(s)

THF: tetrahydrofuran

DMF: dimethylformamide

DCM: dichloromethane.

The melting points are measured on a Kofler plate and the spectral Nuclear Magnetic Resonance values are characterized by the chemical shift calculated with respect to TMS (tetramethylsilane), by the number of protons associated with the signal and by the form of the signal (s for singlet, d for doublet, t for triplet, q for quadruplet, m for multiplet). The operating frequency and the solvent used are indicated for each compound.

The ambient temperature is 20° C.±5° C.

Preparation 1

6-[2-(((3-(1-Methylethyl)phenyl)sulphonyl)amino]-5-(trifluoro-methyl)phenyl]-5-hexynoic acid, methyl ester A solution of 42.90 g (150.39 mM) of methyl ester of 6-[2-amino-5-(trifluoromethyl)phenyl]-5-hexynoic acid in 500 mL of pyridine was prepared and 37.90 g (173.29 mM) of 3-(1-methylethyl)benzenesulphonyl chloride were added. The mixture was stirred at ambient temperature for 15 hours and then poured onto a mixture of ice and hydrochloric acid. The acidic mixture obtained was extracted three times with ethyl acetate. The combined organic phases were dried over magnesium sulphate and concentrated under reduced pressure. The residual oil was purified by chromatography on silica gel, eluting with a cyclohexane/ethyl acetate mixture (9/1; v/v). This gave 29.09 g of the expected compound in the form of an ochre oil (yield=41%).

1H NMR (DMSO-d6, 250 MHz) δ=1.12 (d, J=6.9, 6H), 1.76 (q, J=7.0, 2H), 2.40 (t, J=7.0, 2H), 2.44 (t, J=7.0, 2H), 2.92 (q, J=6.9, 1H), 3.62 (s, 3H), 7.47-7.51 (m, 4H), 7.62-7.66 (m, 3H), 9.68 (s, 1H).

EXAMPLE 1

1-[[3-(1-Methylethyl)phenyl]sulphonyl]-5-(trifluoromethyl)-1H-indole-2-butanoic acid, methyl ester A solution of 28.12 g (60.15 mM) of ester obtained according to Preparation 1 in 250 mL of 1,2-dichloroethane was prepared and 12.49 g (62.55 mM) of (cupric) copper acetate monohydrate were added. The mixture was placed under nitrogen and taken to reflux with stirring for approximately 15 hours. The reaction mixture was filtered and the solid filtration residue was washed on the filter with DCM. The combined filtrates were concentrated under reduced pressure. This gave 27.70 g of the expected compound in the form of beige crystals (yield=99%).

m.p.=115° C.

EXAMPLE 2

1-[[3-(1-Methylethyl)phenyl]sulphonyl]-5-(trifluoromethyl)-1H-indole-2-butanoic acid 27.50 g (58.82 mM) of ester obtained according to Example 1 were mixed with 450 mL of THF, and 4.23 g (176.47 mM) of lithium hydroxide in 100 mL of water were added. The mixture was stirred for approximately 15 hours at ambient temperature and then cooled to 0° C. Then, gradually, 180 mL of N hydrochloric acid were added with thorough stirring. The organic phase was separated and half of the solvent was evaporated without heating, under reduced pressure. The evaporation residue was extracted three times with dichloromethane. The combined organic phases were dried over magnesium sulphate, filtered and concentrated under reduced pressure. This gave 26.22 g of the expected product in the form of a white powder (yield=98%).

m.p.=160° C.

EXAMPLE 2A

1-[[3-(1-Methylethyl)phenyl]sulphonyl]-5-(trifluoromethyl)-1H-indole-2-butanoic acid, sodium salt 68 mg (0.15 mM) of acid obtained according to Example 2 in solution in 4 mL of tetrahydrofuran were mixed with 6 mg (0.15 mM) of sodium hydroxide in solution in 3 mL of water. The mixture was stirred at ambient temperature for 6 hours and then concentrated under reduced pressure. This gave 65 mg of the expected salt in the form of a white crystalline powder (yield=91%).

m.p.=231° C.

EXAMPLE 2B

1-[[3-(1-Methylethyl)phenyl]sulphonyl]-5-(trifluoromethyl)-1. H-indole-2-butanoic acid, piperazine salt 400 mg (0.88 mM) of acid obtained according to Example 2 were dissolved in 10 mL of tetrahydrofuran, and 76 mg (0.88 mM) of piperazine were added. The reaction mixture was stirred overnight at ambient temperature and then concentrated under reduced pressure. This gave 400 mg of the expected salt in the form of a white crystalline powder (yield=46%).

m.p.=147° C.

EXAMPLE 2C

1-[[3-(1-methylethyl)phenyl]sulphonyl]-5-(trifluoromethyl)-1H-indole-2-butanoic acid, tris(hydroxymethyl)aminomethane salt 400 mg (0.88 mM) of acid obtained according to Example 2 were dissolved in 10 mL of tetrahydrofuran, and 106.85 mg (0.88 mM) of tris(hydroxymethyl)aminomethane were added. 3 mL of water were added to give a solution. The reaction mixture was stirred overnight at ambient temperature and then concentrated under reduced pressure. The residue was taken up three times with methanol, the solvent being subsequently stripped off under reduced pressure. This gave 480 mg of the expected salt in the form of a white crystalline powder (yield=95%).

m.p.=126° C.

Preparation 2

6-[5-Chloro-2-[[[3-(1-methylethyl)phenyl]sulphonyl]amino]phenyl]-5-hexynoic acid, methyl ester Proceeding in the same way as for Preparation 1, starting from the methyl ester of 6-(2-amino-5-chlorophenyl)-5-hexynoic acid, the expected compound was obtained in the form of a brown oil (yield=96%).

1H NMR (DMSOd$_6$, 300 MHz) δ=1.13 (d, J=6.9, 6H) 1.71 (q, J=7.1, 2H), 2.33 (t, J=7.1, 2H), 2.42 (t, J=7.4, 2H), 2.91 (q, J=6.9, 1H), 3.61 (s, 3H), 7.26 (d, J=7.3, 1H), 7.34-7.40 (m, 3H), 7.49-7.57 (m, 2H), 7.76-7.78 (m, 1H), 9.68 (s, 1H).

EXAMPLE 3

1-[[3-(1-Methylethyl)phenyl]sulphonyl]-5-chloro-1H-indole-2-butanoic acid, methyl ester A solution of 0.3 g (0.69 mM) of ester obtained according to Preparation 2 in 13 mL of 1,2-dichloroethane was prepared and 0.21 g (1.05 mM) of cupric acetate monohydrate was added. The reaction mixture was irradiated in a microwave oven at 120° C. for 15 minutes, then cooled and filtered. The residue on the filter was washed with DCM and then the filtrate was concentrated under reduced pressure. The crude product was purified by chromatography on silica gel, eluting with a cyclohexane/ethyl acetate mixture (9/1; v/v). This gave 0.23 g of the expected compound in the form of a beige solid (yield=77%).

m.p.=94-97° C.

1H NMR (DMSOd$_6$, 250 MHz) δ=1.11 (d, J=6.9, 6H), 1.95 (q, J=7.4, 2H), 2.42 (t, J=7.4, 2H), 2.94 (q, J=7.4, 1H), 3.02 (t, J=7.4, 2H), 3.59 (s, 3H), 6.61 (s, 1H), 7.32 (dd, J=2.2 and 8.9, 1H), 7.47 (t, J=7.9, 1H), 7.56-7.63 (m, 4H), 8.06 (d, J=8.9, 1H).

EXAMPLE 4

1-[[3-(1-Methylethyl)phenyl]sulphonyl]-5-chloro-1H-indole-2-butanoic acid

Proceeding in a manner similar to that of Example 2, starting from the compound obtained according to Example 3, gave the expected product in the form of a dark beige solid (yield=93%).

m.p.=128° C.

Preparation 3

6-Heptynoic acid, 1,1-dimethylethyl ester 8.00 g (63.41 mM) of 6-heptynoic acid were dissolved in a mixture of 137 mL of anhydrous dichloromethane and 0.70 mL of anhydrous dimethylformamide. 16.10 g (126.83 mM) of oxalyl chloride were added dropwise. The reaction mixture was stirred at ambient temperature for 1 hour under a nitrogen atmosphere and then evaporated under a nitrogen atmosphere. The residual product was taken up in 137 mL of tetrahydrofuran. The mixture was cooled to 0° C. and admixed in portions with 14.23 g (126.83 mM) of potassium tert-butoxide. The reaction mixture was held at ambient temperature with stirring for an hour. Then 200 g of ice and 200 mL of water were added. The mixture was extracted with 3 times 200 mL of ether and then the combined organic phases were dried over magnesium sulphate and concentrated under reduced pressure. This gave 7.46 g of the expected compound in the form of a brown oil (yield=65%).

1H NMR (DMSO-d6, 250 MHz) δ=1.40 (s, 9H), 1.40-1.45 (m, 4H), 2.13-2.22 (m, 4H), 2.75 (t, J=2.7, 1H).

Preparation 4

7-[2-Amino-5-(trifluoromethyl)phenyl]-6-heptynoic acid, 1,1-dimethylethyl ester

A solution of 9.78 g (34.07 mM) of 2-iodo-4-(trifluoromethyl)aniline and 7.45 g (40.89 mM) of the ester of 6-heptynoic acid obtained according to Preparation 3 in 136 mL of triethylamine was prepared. 1.20 g (1.70 mM) of dichlorobis(triphenylphosphine)palladium and 0.3 g (1.70 mM) of cuprous iodide were added. The reaction mixture was stirred and heated at reflux under a nitrogen atmosphere for 3 hours, and then concentrated under reduced pressure. The evaporation residue was taken up in ethyl acetate and washed with sodium hydrogencarbonate solution (approx. 1 M in water), then with 1 N hydrochloric acid and finally with distilled water. The organic phase was dried over magnesium sulphate, filtered and concentrated under reduced pressure. This gave 12.38 g of the expected compound in the form of a brown oil (yield=71%).

$^1$H NMR (DMSOd$_6$, 250 MHz) δ=1.40 (s, 9H), 1.53-1.68 (m, 4H), 2.24 (t, J=8.4, 2H), 2.48 (t, J=8.1, 2H), 5.93 (s, 2H), 6.78 (d, J=10.2, 1H), 7.28-7.33 (m, 2H).

Preparation 5

5-Trifluoromethyl-1H-indole-2-pentanoic acid, 1,1-dimethylethyl ester

A solution of 7.63 g (22.35 mM) of tert-butyl ester of 7-[2-amino-5-(trifluoromethyl)phenyl]-6-heptynoic acid in 44.70 mL of 1,2-dichloroethane was prepared and 6.69 g (33.52 mM) of cupric acetate monohydrate were added. The mixture was taken to reflux with stirring for 48 hours. The reaction mixture was filtered on a nylon filter and then the filtrate was concentrated under reduced pressure. The crude product was purified by chromatography on silica gel, eluting with a cyclohexane/ethyl acetate mixture (9/1; v/v). This gave 3.42 g of the expected compound in the form of a yellow powder (yield=45%).

1H NMR (DMSOd$_6$, 250 MHz) δ=1.38 (s, 9H), 1.51-1.57 (m, 2H), 1.67-1.73 (m, 2H), 2.23 (t, J=8.4, 2H), 2.75 (t, J=8.7, 2H), 6.31 (s, 1H), 7.28 (dd, J=2.1 and 10.2, 1H), 7.44 (d, J=10.2, 1H), 7.79 (s, 1H).

EXAMPLE 5

1-[[3-(1-Methylethyl)phenyl]sulphonyl]-5-(trifluoromethyl)-1H-indole-2-pentanoic acid, 1,1-dimethylethyl ester 46.87 mg (1.17 mM) of sodium hydride (60% in oil) were added to a solution of 200.00 mg (0.59 mM) of ester obtained according to Preparation 5 in 0.5 mL of DMF, at 0° C. This mixture was stirred for 5 minutes and, still at 0° C., a solution of 192.20 mg (0.88 mM) of 3-(1-methylethyl)benzenesulphonyl chloride in 0.5 mL of DMF was added. The mixture was stirred at ambient temperature for 3 hours and then ammonium chloride solution was added to neutralize the traces of sodium hydride. The mixture was extracted with dichloromethane. The organic phase was concentrated under reduced pressure and then the resulting reaction mixture was reacted in the next step without purification.

EXAMPLE 6

1-[[3-(1-Methylethyl)phenyl]sulphonyl]-5-(trifluoromethyl)-1H-indole-2-pentanoic acid A solution of 200.00 mg (0.38 mM) of ester obtained according to Example 5 in 1 mL of DCM was prepared and 1 mL of trifluoroacetic acid was added. The reaction mixture was stirred at ambient temperature for 3 hours and then taken up in DCM and concentrated under reduced pressure. The crude product was purified by chromatography on silica gel, eluting with a cyclohexane/ethyl acetate mixture (6/4; v/v). This gave 50.00 mg of the expected compound in the form of an off-white powder (yield=26%).

m.p.=119° C.

Preparation 6

3-(1,1-Dimethylethyl)-N-[2-iodo-4-(trifluoromethyl)phenyl]benzene-sulphonamide A solution of 1.03 g (3.59 mM) of 2-iodo-4-(trifluoromethyl)aniline in 5 mL of pyridine was prepared and 1.00 g (4.31 mM) of 3-(1,1-dimethylethyl)benzene-sulphonyl chloride was added. The reaction mixture was subsequently stirred at ambient temperature for 4 hours. The reaction mixture was washed with 1N hydrochloric acid and extracted twice with ethyl acetate. The organic phase was dried over magnesium sulphate and then filtered and concentrated under reduced pressure. The crude product was purified by chromatography on silica gel, eluting with a cyclohexane/ethyl acetate mixture (gradient from 100/0 to 90/10; v/v). This gave 730 mg of the expected compound in the form of a white crystalline powder (yield=42%).

m.p.=111° C.

EXAMPLE 7

1-[[3-(1,1-Dimethylethyl)phenyl]sulphonyl]-5-(trifluoromethyl)-1H-indole-2-butanoic acid, methyl ester Under nitrogen a mixture of 250 mg (0.52 mM) of the compound obtained according to Preparation 6, 4.93 mg (0.03 mM) of cuprous iodide, 9.08 mg (0.01 mM) of bis(triphenylphosphine)dichloropalladium and 3 mL of triethylamine was prepared. The reaction mixture was stirred at ambient temperature for 10 minutes. 120.31 mg (0.95 mM) of methyl ester of 5-hexynoic acid in solution in 3 mL of dimethylformamide were added. The reaction mixture was heated at reflux for 3 hours and then washed with water and extracted with ethyl acetate. The organic phase was dried over magnesium sulphate and concentrated under reduced pressure. The crude product was purified by chromatography on silica gel, eluting with a cyclohexane/ethyl acetate mixture (95/5; v/v). This gave 115 mg of the expected product in the form of a beige crystalline powder (yield=46%).

m.p.=84° C.

EXAMPLE 8

1-[[3-(1,1-Dimethylethyl)phenyl]sulphonyl]-5-(trifluoromethyl)-1H-indole-2-butanoic acid Proceeding in the same way as for Example 2, starting from the compound obtained according to Example 7, gave the expected product in the form of a white powder (yield=27%).

m.p.=135-141° C.

EXAMPLE 9

1-[[3-(1,1-Dimethylethyl)phenyl]sulphonyl]-5-(trifluoromethyl)-1H-indole-2-pentanoic acid, methyl ester Under nitrogen a mixture of 57.93 g (119.87 mM) of the compound obtained according to Preparation 6 and 350 mL of dimethylformamide was prepared and was stirred until the product was fully dissolved. Then, in succession, 21.84 g (155.83 mM) of methyl ester of 4-pentynoic acid, 1.14 g (5.99 mM) of cuprous iodide and 1.68 g (2.40 mM) of bis(triphenylphosphine)dichloropalladium were added. This mixture was stirred at ambient temperature for 15 minutes and then admixed dropwise with 174 mL of triethylamine. The reaction mixture was heated for 14 hours at 80° C., cooled, then hydrolysed with 1 L of water and extracted with ethyl acetate. The organic phase was dried over magnesium sulphate, filtered and concentrated under reduced pressure. The oily product obtained was dissolved at 40° C. in isopropyl ether. The solution obtained was filtered and concentrated under reduced pressure. The product obtained was recrystallized from a mixture of 140 mL of isopropanol and 60 mL of water. This gave 46.51 g of the expected product in the form of an off-white solid (yield=78%).

m.p.=77° C.

EXAMPLE 10

1-[[3-(1,1-Dimethylethyl)phenyl]sulphonyl]-5-(trifluoromethyl)-1H-indole-2-pentanoic acid Proceeding in the same way as for Example 2, starting from the compound obtained according to Example 9, gave the expected product in the form of an off-white solid (yield=94%).

m.p.=135° C.

The compounds according to the invention that are described above have been set out in the table below:

TABLE I

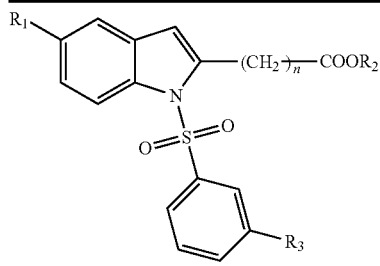

| Ex. | $R_1$ | n | $R_2$ | $R_3$ |
|---|---|---|---|---|
| 1 | 5-$CF_3$ | 3 | $CH_3$ | $CH(CH_3)_2$ |
| 2 | 5-$CF_3$ | 3 | H | $CH(CH_3)_2$ |
| 3 | 5-Cl | 3 | $CH_3$ | $CH(CH_3)_2$ |
| 4 | 5-Cl | 3 | H | $CH(CH_3)_2$ |
| 5 | 5-$CF_3$ | 4 | $C(CH_3)_3$ | $CH(CH_3)_2$ |
| 6 | 5-$CF_3$ | 4 | H | $CH(CH_3)_2$ |
| 7 | 5-$CF_3$ | 3 | $CH_3$ | $C(CH_3)_3$ |
| 8 | 5-$CF_3$ | 3 | H | $C(CH_3)_3$ |
| 9 | 5-$CF_3$ | 4 | $CH_3$ | $C(CH_3)_3$ |
| 10 | 5-$CF_3$ | 4 | H | $C(CH_3)_3$ |

Pharmacological Activity

The compounds of the invention were subjected to biological tests in order to evaluate their potential to treat or prevent certain neurodegenerative pathologies.

To start with, using an in vitro assay, the capacity of the compounds according to the invention to behave as an activator of the heterodimers formed by the NURR-1 nuclear receptor and the RXR nuclear receptors was measured.

A transactivation assay was used as a primary screening test. Cos-7 cells were co-transfected with a plasmid expressing a chimera of the human receptor NURR-1-Gal4, a plasmid expressing the RXR human receptor (RXRα or RXRγ receptor) and a reporter plasmid 5Gal4pGL3-TK-Luc. The transfections were carried out using a chemical agent (Jet PEI).

The transfected cells were distributed in 384-well plates and left to stand for 24 hours.

After 24 hours, the culture medium was changed. The test products were added (final concentration between $10^{-4}$ and $3.10^{-10}$ M) in the culture medium. After incubation overnight, the expression of luciferase was measured after addition of "SteadyGlo" in accordance with the manufacturer's (Promega) instructions.

4-[[6-Methyl-2-phenyl-5-(2-propenyl)-4-pyrimidinyl]amino]benzoic acid (called XCT0135908) at $2\times10^{-5}$ M (RXR agonist) was used as reference.

The levels of induction were calculated in relation to the basal activity of each heterodimer. The results were expressed as a percentage of the level of induction relative to the level of induction obtained with the reference (the level of induction of the reference is arbitrarily equal to 100%).

The compounds according to the invention exhibit a level of induction of up to 104% (NURR1/RXRα) and 88% (NURR1/RXRγ . . . ) and EC50 values of down to 26 nM (NURR1/RXRα) and 20 nM (NURR1/RXRγ . . . ).

Some compounds according to the invention have an $EC_{50}$ of less than 100 nM, especially on the NURR-1/RXRα heterodimer.

By way of example, among the compounds according to the invention, the comparative results below are obtained, expressed as a percentage relative to a reference NURR-1/RXR activator compound (XCT0135908):

| | hNurr1_RXRγFL | | hNurr1_RXRαFL | |
|---|---|---|---|---|
| Compound | $EC_{50}$ (nM) | Eff (%) | $EC_{50}$ (nM) | Eff (%) |
| Example 2 | 113 | 79 | 73 | 86 |
| Example 8 | 20 | 70 | 26 | 100 |
| Example 10 | 77 | 88 | 55 | 104 |
| Comparative example* | 1108 | 74 | 571 | 75 |

*Example 76 of patent application WO 2007/026097
Eff: efficacy in % relative to the reference XCT0135908

As a comparison, a study was also made of Example 76 of patent application WO 2007/026097, with a structure relatively close to that of the compounds according to the invention, and for which the results show that the concentration at which the compound gives half of the maximum efficacy ($EC_{50}$) is at least 10 times greater than that of the compounds described in the invention.

A first series of tests in vivo was performed with a number of compounds according to the invention, with the aim of determining their cerebral and plasma pharmacokinetic profile in the male C57Bl6 mouse and hence of verifying that the compounds pass the blood-brain barrier.

The protocol used was as follows:

Male C57Bl6 mice (25-30 g) from Janvier, Le Genest-St-Isle, France, were used for this study (12 mice per dose).

The animals were fed with standard rodent feed (Purina Mills, St. Louis, Mo.), and were placed in cages and subjected to 12 h/12 h light/dark cycles, the room temperature being maintained at 22±2° C. and the humidity level at 55±10%.

The mice were not fasted before administration. Water was supplied ad libitum throughout the study.

The test compound was administered orally at 10 mg/kg.

For oral administration at 10 mg/kg, the animals were fed by gavage with 10 mL/kg of a suspension of the test compound, prepared in 1% methylcellulose 400 cp.

The animals were sacrificed under anaesthesia at times 15 min, 30 min, 1 h, 3 h, 6 h and 8 h after gavage.

At each time, and on each sacrificed animal, the blood was collected and the brain was removed.

1 mL of blood collected in 1.5 mL tubes containing 20 μL of evaporated anticoagulant (solution of sodium heparinate at 1000 UI/mL) was centrifuged at 4500 g for 3 min to give approximately 400 μL of plasma. The plasma was divided into 2 aliquots of 200 μL, which were stored at −20° C. until extraction by protein precipitation, followed by analysis by liquid chromatography coupled with tandem mass spectrometry (LC-MS/MS) for the quantification of the test compound.

Immediately after their removal, the brains were plunged into liquid nitrogen and then stored at −20° C. for analysis. The brains were subsequently ground in the presence of aqueous/organic solvent mixture to give a homogenate. These homogenates were subsequently centrifuged and the test compound was extracted from the resulting supernatant, by liquid-liquid extraction, and then quantified by LC-MS/MS.

The pharmacokinetic parameters were determined on the basis of a non-compartmental approach in Excel. The area under the curve ($AUC_{0-t}$) was determined by the linear trapezoidal method.

As an example, the results obtained with the compounds of Examples 2, 8 and 10 were as follows:

| Compound | PK data after oral administration: 10 mg/kg in mice | |
|---|---|---|
| | $AUC_{brain}$ | Ratio $AUC_{brain}/AUC_{plasma}$ |
| Example 2 | 3318 | 0.67 |
| Example 8 | 2371 | 0.87 |
| Example 10 | 1689 | 0.80 |

A second series of tests in vivo was performed with the compounds according to the invention, with the aim of verifying that the molecules do possess the expected neuroprotective effect.

The compound of Example 2 was tested on a model of mice treated with 1-methyl-4-phenyl-1,2,3,6-tetrahydropyridine (MPTP), in order to confirm its potential activity. MPTP is a neurotoxin which gives rise to permanent symptoms of Parkinson's disease by destroying certains neurons in the substantia nigra of the brain. The protocol used was as follows.

Male C57BL6/J mice, aged 10-12 weeks at the beginning of the studies, were divided into groups of 8 animals. The compound was administered orally and twice daily for 11 days in total. Administration was commenced 3 days before treatment with the MPTP toxin at 20 or 25 mg/kg. MPTP was administered once daily by intraperitoneal injection for 5 days. The administration of the test compound was continued for 3 days after the treatment with MPTP. One group of mice received the vehicle alone (0.5% methylcellulose solution). The animals were euthanized after the final gavage, and the striatum was removed. The dopamine was extracted from the striatum, and the amount of dopamine (DA), expressed in ng per g of striatum (mean±SEM), was measured by high-performance liquid chromatography (HPLC) with electrochemical detection.

Figure 2:
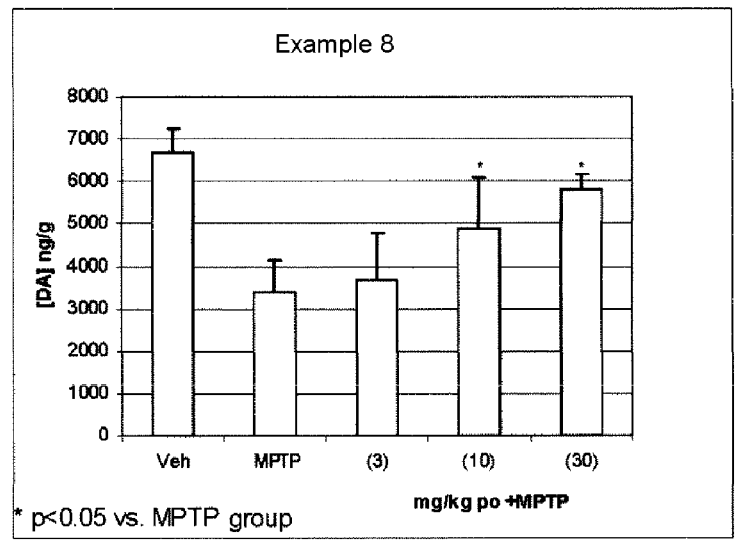
Figure 3:
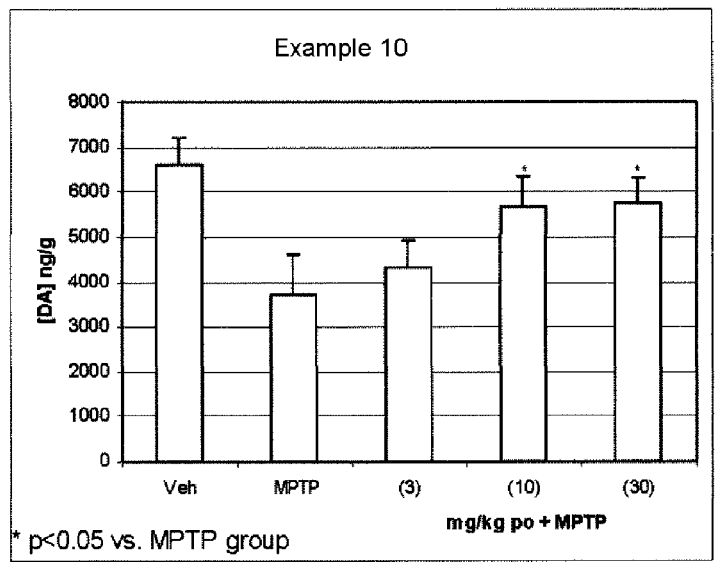

The results obtained were reported in attached FIGS. 1 to 3.

These results show that the administration of MPTP gives rise to a characteristic reduction in the level of dopamine in the striatum, and that the compounds according to Examples 2, 8 and 10 reduce, in a dose-dependent way, the action of MPTP, a toxin which gives rise to a Parkinsonian syndrome.

Hence a significant effect is observed at doses of 10 and 30 mg/kg: the compounds of the invention, administered orally, are capable of re-establishing the dopaminergic activity inhibited by MPTP within the brain.

Compounds of this kind, which cross the blood-brain barrier and possess a favourable effect on communication between the neurons, may advantageously be used as an active principle in a medicament intended for the treatment of Parkinson's disease.

These results in vitro and in vivo show that the compounds of the invention are capable of modifying the mechanisms of the disease in certain animal and cell models, and of halting the degenerative process by giving rise to neuroprotective agents which combat the cell death of the dopaminergic neurons. The results thus confirm the interest of these compounds in respect of their use as active principles of medicaments intended for the prevention or treatment of neurodegenerative diseases, and more particularly of Parkinson's disease.

The invention likewise provides a pharmaceutical composition comprising as active principle at least one compound of the formula (I), or one of its pharmaceutically acceptable salts.

In another aspect, the present application aims to embrace the use of a pharmaceutical composition of this kind for the prevention or treatment of diseases involving the NURR-1 receptor, especially neurodegenerative diseases, and more particularly Parkinson's disease.

These pharmaceutical compositions may be prepared conventionally, using pharmaceutically acceptable excipients, to give forms which can be administered parenterally or, preferably, orally, such as, for example, tablets or capsules.

In the case of injectable forms, it would be advantageous to use the compounds of formula (I) in the form of salts which are soluble in an aqueous medium. As indicated above, the salts are preferably formed between a compound of formula (Ib) (acid) and a pharmacologically acceptable non-toxic base. The formulation may be either a solution of the compound in an isotonic aqueous medium in the presence of soluble excipients, or a lyophilizate of the compound, to which the dilution solvent is added extemporaneously. These preparations can be injected in perfusion form or as a bolus, depending on the needs of the patient.

From a practical standpoint, in the case of administration of the compound parenterally, the daily dose in humans will be preferably between 2 and 250 mg.

The preparations which can be administered orally will preferably be presented in the form of a capsule or tablet containing the finely ground or, better still, micronized compound of the invention, mixed with excipients which are known to a person skilled in the art, such as, for example, lactose, pregelatinized starch and magnesium stearate.

For example, a mixture composed of 500 g of the compound of Example 2, finely ground, 500 g of pregelatinized starch, 1250 g of lactose, 15 g of sodium lauryl sulphate and 235 g of polyvinylpyrrolidone was granulated. This granulated mixture was subsequently added to 20 g of magnesium stearate and 80 g of microcrystalline cellulose, and the resulting mixture was distributed, after grinding and screening, into 260 mg capsules. This gave capsules each containing 50 mg of active principle.

From a practical standpoint, in the case of administration of the compound orally, the daily dose in humans will be preferably between 5 and 500 mg.

The invention claimed is:
1. A compound selected from the group consisting of
i) compounds of formula (I)

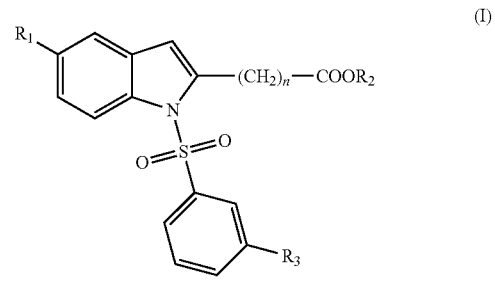

in which
$R_1$ represents a trifluoromethyl group,
$R_2$ represents a hydrogen atom or a $C_1$-$C_4$ alkyl group,
$R_3$ represents an isopropyl group or a tert-butyl group and
n=3 or 4
and
ii) pharmaceutically acceptable salts of said compounds of formula (I).
2. A compound according to claim 1, wherein $R_3$ represents an isopropyl group.

3. A compound according to claim 1, wherein $R_3$ represents a tert-butyl group.

4. A compound according to claim 1, wherein $R_2$ represents a hydrogen atom.

5. A pharmaceutical composition comprising at least one compound according to claim 1 and at least one pharmaceutically acceptable excipient.

6. A method of treating or inhibiting a disease involving the NURR-1 receptor in a subject, said method comprising administering to said subject a pharmacologically effective amount of a compound according to claim 1, wherein said disease involving the NURR-1 receptor is Parkinson's disease.

7. A compound according to claim 1, selected from the group consisting of:
- 1-[[3-(1-Methylethyl)phenyl]sulfonyl]-5-(trifluoromethyl)-1H-indole-2-butanoic acid;
- 1-[[3-(1,1-Dimethylethyl)phenyl]sulphonyl]-5-(trifluoromethyl)-1H-indole-2-butanoic acid; and
- 1-[[3-(1,1-Dimethylethyl)phenyl]sulphonyl]-5-(trifluoromethyl)1H-indole-2-pentanoic acid.

8. A pharmaceutical composition according to claim 5, wherein said compound is selected from the group consisting of:
- 1-[[3-(1-Methylethyl)phenyl]sulfonyl]-5-(trifluoromethyl)-1H-indole-2-butanoic acid;
- 1-[[3-(1,1-Dimethylethyl)phenyl]sulphonyl]-5-(trifluoromethyl)-1H-indole-2-butanoic acid; and
- 1-[[3-(1,1-Dimethylethyl)phenyl]sulphonyl]-5-(trifluoromethyl)1H-indole-2-pentanoic acid.

9. A method according to claim 6, wherein said compound is selected from the group consisting of:
- 1-[[3-(1-Methylethyl)phenyl]sulfonyl]-5-(trifluoromethyl)-1H-indole-2-butanoic acid;
- 1-[[3-(1,1-Dimethylethyl)phenyl]sulphonyl]-5-(trifluoromethyl)-1H-indole-2-butanoic acid; and
- 1-[[3-(1,1-Dimethylethyl)phenyl]sulphonyl]-5-(trifluoromethyl)1H-indole-2-pentanoic acid.

\* \* \* \* \*

UNITED STATES PATENT AND TRADEMARK OFFICE
CERTIFICATE OF CORRECTION

PATENT NO.        : 8,575,210 B2
APPLICATION NO. : 13/003554
DATED             : November 5, 2013
INVENTOR(S)       : Boubia et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 187 days.

Signed and Sealed this

Twenty-second Day of September, 2015

Michelle K. Lee
*Director of the United States Patent and Trademark Office*